(12) United States Patent
Ikonomidou (10) Patent No.: US 7,247,610 B2
(45) Date of Patent: Jul. 24, 2007

(54) USE OF GLUTAMATE ANTAGONISTS FOR THE TREATMENT OF CANCER

(76) Inventor: Hrissanthi Ikonomidou, Joersstrasse 16, D-13505 Berlin (DE)

( * ) Notice: Subject to any disclaimer, the term of this patent is extended or adjusted under 35 U.S.C. 154(b) by 0 days.

(21) Appl. No.: 10/912,159

(22) Filed: Aug. 6, 2004

(65) Prior Publication Data

US 2005/0054619 A1  Mar. 10, 2005

Related U.S. Application Data

(62) Division of application No. 09/830,354, filed on Apr. 25, 2001, now Pat. No. 6,797,692.

(51) Int. Cl.
*A61K 31/00* (2006.01)
*C07D 237/26* (2006.01)

(52) U.S. Cl. .................. 514/2; 514/80; 514/247; 514/258; 424/9.1

(58) Field of Classification Search .............. 514/2, 514/80, 247; 530/300, 350
See application file for complete search history.

(56) References Cited

U.S. PATENT DOCUMENTS 5,958,930 A * 9/1999 Gangjee .................. 514/265.1
6,046,180 A * 4/2000 Jackson et al. ............... 514/75

OTHER PUBLICATIONS

Fletcher, E. and Lodge, D., Pharm. Ther. vol. 70, No. 1, pp. 65-89, 1996.*
Xue, D. et al. (ABSTRACT) (J. Cereb Blood Flow Metab. 1994).*
Turski, L. et al. PNAS 95: 10960-10965 (1998).*
Browne SE and McCulloch J (ABSTRACT) (Brain Res. 1994).*
Elting, J-W. et al. Stroke 33: 2813-2818 (2002).*
Paternain et al. Neuron 14: 185-189 (1995).*

* cited by examiner

*Primary Examiner*—Robert A. Wax
*Assistant Examiner*—Anand Desai
(74) *Attorney, Agent, or Firm*—Millen, White, Zelano & Branigan, P.C.

(57) ABSTRACT

Disclosed are methods for treating cancer by administering an inhibitor of the interaction of glutamate with the KA receptor complex.

15 Claims, 5 Drawing Sheets

USE OF GLUTAMATE ANTAGONISTS FOR THE TREATMENT OF CANCER

This application is a divisional of U.S. patent application Ser. No. 09/830,354, filed Apr. 25, 2001, which is now granted U.S. Pat. No. 6,797,692.

BACKGROUND ART

Glutamate is a major neurotransmitter but possesses also a wide metabolic function in the body. It is released from approximately 40% of synaptic terminals and mediates many physiological functions by activation of different receptor types (Watkins and Evans (1981) Excitatory amino acid transmitters, Annu. Rev. Pharmacol., 21: 165-189; Gasic and Hollmann (1992) Molecular neurobiology of glutamate receptors, Annu. Rev. Physiol., 54: 507-536). Two main categories of glutamate receptors have been identified, ionotropic and metabotropic (Bettler and Mulle, (1995) Neurotransmitter Receptors II, AMPA and Kainate Receptors, Neuropharmacology, 34: 123-139; Pin and Duvoisin (1995) Neurotransmitter receptors I, The Metabotropic Glutamate Receptors: Structure and Functions, Neuropharmacology, 34: 1-26; Mori and Mishina (1995) Neurotransmitter Receptors VIII, Structure and Function of the NMDA Receptor Channel, Neuropharmacology, 34: 1219-1237). Ionotropic glutamate receptors can be subdivided into N-methyl-D-aspartate (NMDA), α-amino-3-hydroxy-5-methyl-4-isoxazole-propionate (AMPA), and kainate receptors. Metabotropic glutamate receptors can be subdivided into three classes, mGluRI, mGluRII and mGluRIII (Pin and Duvoisin (1995) Neurotransmitter receptors I, The Metabotropic Glutamate Receptors: Structure and Functions, Neuropharmacology, 34: 1-26). Five receptor subunits form the functional NMDA receptor which is modulated by glycine and polyamines and blocked by $Mg^{2+}$. Activation of NMDA receptors leads to influx of $Na^+$- and $K^+$-ions into the cell as well as $Ca^{2+}$-ions, either through the receptor channel itself or through voltage dependent $Ca^{2+}$-channels (Bettler and Mulle, (1995) Neurotransmitter Receptors II, AMPA and Kainate Receptors, Neuropharmacology, 34: 123-139; Mori and Mishina (1995) Neurotransmitter Receptors VIII, Structure and Function of the NMDA Receptor Channel, Neuropharmacology, 34: 1219-1237). Four different subunits, named GluR1-GluR4, form the AMPA receptor channel. AMPA receptors are highly permeable to $Na^+$- and $K^+$-ions. AMPA receptor assemblies lacking the GluR2 subunit are also permeable to $Ca^{2+}$-ions (Hollmann M, Heinemann S (1994): Cloned glutamate receptors, Annu. Rev. Neurosci., 17: 31-108).

Kainate receptors are built from five subunits, GluR5-7 as well as KA1 and KA2. Kainate receptor associated ion channels are permeable to $Na^+$- and $K^+$-ions as well as $Ca^{2+}$. $Ca^{2+}$-permeability of kainate receptor associated ion channels is dependent on the presence of the GluR6 subunit within the receptor complex (Hollmann M, Heinemann S (1994): Cloned glutamate receptors, Annu. Rev. Neurosci., 17: 31-108). There is considerable experimental and clinical evidence indicating that glutamate is involved in the pathogenesis of neuronal degeneration in the context of hypoxia/ischemia and trauma of the central nervous system, seizures and hypoglycemia. In addition, glutamate is thought to be involved in the pathogenesis of chronic neurodegenerative disorders, such as amyotrophic lateral sclerosis, Huntington's, Alzheimer's and Parkinson's disease. Functional glutamate receptors have been also identified in lung, muscle, pancreas and bone (Mason D J, Suva L J, Genever P G, Patton A J, Steuckle S, Hillam R A, Skerry T M (1997) Mechanically regulated expression of a neural glutamate transporter in bone: a role for excitatory amino acids as osteotropic agents? Bone 20: 199-205; Patton A J, Genever P G, Birch M A, Suva L J, Skerry T M (1998) Expression of an N-methyl-D-aspartate-type receptor by human and rat osteoblasts and osteoclasts suggests a novel glutamate signaling pathway in bone, Bone 22; 645-649). However, no link has been established so far between glutamate receptor stimulation and tumor growth.

Many forms of cancer have been described affecting every form of tissue known in man. Of the described forms of human cancer, none is curable in 100% of the affected patients. Treatment modes include surgical removal, chemotherapy with cytostatic agents alone or in combination with hormone receptor modulators and/or steroids and/or interferons, and radiation (Hill R (1992): Cellular basis for radiotherapy, in The Basic Science of Oncology, McGraw-Hill, pp. 259-275).

I. The term inhibitor of the interaction of glutamate with the AMPA receptor complex applies to:

1. all agents that bind to the AMPA receptor and prevent or reduce the binding of glutamate to the AMPA binding site in a competitive- or non-competitive manner. These are antagonists of the binding of glutamate to the AMPA receptor;

2. all agents that do not bind to the AMPA receptor binding site but bind or interact with AMPA receptor modulatory sites and thus prevent glutamate from triggering the signal that would occur when glutamate binds to the AMPA binding site;

3. all agents that interact directly with the AMPA-ion channel, i.e. AMPA receptor channel blockers. These agents reduce permeability of the ion channels associated with the AMPA receptor to ions (preferably $Na^+$, $K^+$ and/or $Ca^{2+}$);

4. all agents that decrease the release of glutamate from nerve endings or other tissues and thus prevent glutamate from binding to the AMPA binding sites and from triggering the signal that would occur as a result of binding of glutamate to AMPA binding site;

5. all agents that decrease synthesis of glutamate and thus prevent glutamate from binding to its binding sites;

6. all agents that increase the metabolism of glutamate and therefore prevent glutamate from triggering the signal that would occur as a result of binding of glutamate to its binding sites;

7. all agents that increase the uptake of glutamate and thus decrease the binding of glutamate to AMPA binding site;

8. all agents that interfere with glutamate transporter systems and decrease the concentration of glutamate in synaptic cleft and thus prevent glutamate from triggering the signal that would occur as a result of binding of glutamate to its binding sites;

9. all agents that interact with glutamate and prevent its binding to the AMPA receptor. Such compounds include i.e. glutamate partial agonists or molecules binding to glutamate;

10. antibodies to AMPA receptor subunits, or to the AMPA receptor, or to glutamate decreasing the binding of glutamate to AMPA binding site.

II. The term inhibitor of the interaction of glutamate with the KA receptor complex applies to:

1. all agents that bind to the KA receptor and prevent or reduce the binding of glutamate to the KA binding site in a competitive- or non-competitive manner. These are antagonists of the binding of glutamate to the KA receptor;

2. all agents that do not bind to the KA receptor binding site but bind or interact with KA receptor modulatory sites and thus prevent glutamate from triggering the signal that would occur when glutamate binds to the KA binding site;

3. all agents that interact directly with the KA-Ion channel, i.e. KA receptor channel blockers. These agents reduce permeability of the ion channels associated with the KA receptor to ions (preferably $Na^+$, $K^+$ and/or $Ca^{2+}$).

4. all agents that decrease the release of glutamate from nerve endings or other tissues and thus prevent glutamate from binding to the KA binding sites and from triggering the signal that would occur as a result of binding of glutamate to KA binding site;

5. all agents that decrease synthesis of glutamate and thus prevent glutamate from binding to its binding sites;

6. all agents that increase the metabolism of glutamate and therefore prevent glutamate from triggering the signal that would occur as a result of binding of glutamate to its binding sites;

7. all agents that increase the uptake of glutamate and thus decrease the binding of glutamate to KA binding site;

8. all agents that interfere with glutamate transporter systems and decrease the concentration of glutamate in synaptic cleft and thus prevent glutamate from triggering the signal that would occur as a result of binding of glutamate to its binding sites;

9. all agents that interact with glutamate and prevent its binding to the KA receptor. Such compounds include e.g. glutamate partial agonists or molecules binding to glutamate;

10. antibodies to KA receptor subunits, or to the KA receptor, or to glutamate decreasing the binding of glutamate to KA binding site.

III. The term inhibitor of the interaction of glutamate with the NMDA/glycine/polyamine receptor complex applies to:

1. all agents that bind to the NMDA receptor or NMDA ion channel associated glycine or polyamine binding site and prevent or reduce the binding of glutamate to the NMDA binding site in a competitive- or non-competitive manner. These are antagonists of the interaction of glutamate with the NMDA receptor;

2. all agents that do not bind to the NMDA receptor binding site but bind or interact with NMDA receptor modulatory sites and thus prevent glutamate from triggering the signal that would occur when glutamate binds to the NMDA binding site;

3. all agents that interact directly with the NMDA-ion channel, i.e. NMDA receptor channel blockers. These agents reduce permeability of the ion channels associated with the NMDA receptor to ions (preferably $Na^+$, $K^+$ and $Ca^{2+}$).

4. all agents that decrease the release of glutamate from nerve endings or other tissues and thus prevent glutamate from binding to the NMDA binding sites and from triggering the signal that would occur as a result of binding of glutamate to NMDA binding site;

5. all agents that decrease synthesis of glutamate and thus prevent glutamate from binding to NMDA and NMDA channel associated binding sites;

6. all agents that increase the metabolism of glutamate and therefore prevent glutamate from triggering the signal that would occur as a result of binding of glutamate to NMDA and NMDA channel sites;

7. all agents that increase the uptake of glutamate and thus decrease the binding of glutamate to NMDA binding site;

8. all agents that interfere with glutamate transporter systems and decrease the concentration of glutamate in synaptic cleft and thus prevent glutamate from triggering the signal that would occur as a result of binding of glutamate to NMDA binding sites;

9. all agents that interact with glutamate and prevent its binding to the NMDA receptor. Such compounds include e.g. glutamate partial agonists or molecules binding to glutamate;

10. antibodies to NMDA receptor subunits, or to the NMDA receptor, or to glutamate decreasing the binding of glutamate to NMDA binding site.

Various glutamate antagonists and receptor channel blockers that are within the scope of the present invention will now be described in greater detail:

A. AMPA Receptor Antagonists

AMPA receptor antagonists refer to compounds that bind to AMPA receptors in a competitive manner or interact with AMPA receptor associated sites and block AMPA mediated signal in a non-competitive manner.

Such antagonists include L-glutamate derivatives, amino alkanoic acid derivatives, α-amino-3-hydroxy-5-methyl-4-isoxazolepropionate derivatives, acetyl-aminophenyl-dihydro-methyl-dioxolo-benzodiazepine, acid amide derivatives, amino-phenyl-acetic acid, 2,3-benzodiazepin-4-one, alkoxy-phenyl-benzodiazepine, amino- or desamino-2,3-benzodiazepine, benzothiadiazine, β-carboline-3-carboxylic acid, fused cycloalkylquinoxalinediones, decahydroisoquinoline, 4-hydroxypyrrolone, 4-hydroxy-pyrrolo-pyridazinone, imidazo-pyrazinone, imidazolo-quinoxalinone, indeno-pyrazine-carboxylic acid, indeno-pyrazinone, indoloneoxime, indolo-pyrazinone, isatine, isatinoxime, oxadiazole, phenyl-azolophthalazine, phenylpyridazino-indole-1,4-dione, quinoline, quinolinone, quinoxaline, quinoxalinedione, quinazolinone, quinolone, nitroquinolone, and sulphamate derivatives.

B. AMPA Receptor Channel Blockers

AMPA receptor channel blockers refer to compounds that reduce the permeability of channels associated with the AMPA receptor to cations (preferably to $Na^+$, $K^+$ and/or $Ca^{2+}$ ions). AMPA receptor channel blockers can therefore be used to prevent a signal being transmitted due to ionic flux that would otherwise occur when glutamate binds to the AMPA receptor.

AMPA receptor channel blockers include e.g. fluorowillardiine, Joro spider toxin, NSTX spider toxin, argiotoxin.

C. KA Receptor Antagonists

KA receptor antagonists refer to compounds that bind to KA receptors in a competitive manner or interact with KA receptor associated sites and block KA mediated signal in a non-competitive manner.

Such antagonists include L-glutamate derivatives, kainic acid derivatives, acid amide derivatives, aminoalkanoic acid derivatives, aminophenyl(alkyl)acetic acid derivatives, fused cycloalkylquinoxalinediones, quinoxalinedione, imidazolo-quinoxalinone, isatine, phenyl-azolophthalazine, pyridothiazines, 4-phosphonoalkyl-quinolinone, quinolinone, quinazoline, quinazolinedione, quinoxalinedione and sulphamate derivatives.

D. KA Receptor Channel Blockers

KA receptor channel blockers refer to compounds that reduce the permeability of channels associated with the KA receptor to cations (preferably to $Na^+$, $K^+$ and/or $Ca^{2+}$ ions). KA receptor channel blockers can therefore be used to prevent a signal being transmitted due to ionic flux that would otherwise occur when glutamate binds to the KA receptor.

KA receptor channel blockers include i.e. Joro spider toxin, NSTX spider toxin and argiotoxin 636.

E. NMDA/Glycine/Polyamine Receptor Antagonists

NMDA/glycine receptor antagonists refer to compounds that bind to NMDA receptors in a competitive manner or interact with NMDA receptor associated sites and block NMDA mediated signal in a non-competitive manner.

Such antagonists include L-glutamate derivatives, tetrahydroquinolines, imidazoloquinoxalinones, isatines, fused cycloalkylquinoxalinediones, quinoxalines, spermine, 4-hydroxy-3-nitro-1,2-dihydroquinolon-2-one derivatives, indole derivatives, benzo-thiadiazine dioxide derivatives, indeno(1,2-b)pyrazin-3-ones or corresponding 2,3-diones, quinoline derivatives, ethyl(phenyl-carbamoyl)-ethenyl) dichloroindole carboxylates, thienopyrazine 2,3-dione derivatives, 2-(2,3-dicarboxycyclopropyl) glycine, 2-amino-3-substituted phenyl propionic acid derivatives, 1-carboxyalkylquinoxaline-2.3(1H,4H)dione derivatives, thienyl-glycine derivatives, benzo-fused azacyclic compounds, tricyclic quinoxaline-diene derivatives, 3-hydroxy anthranilic acid and salts, decahydroisoquinolines, tri- or tertasubstituted guanidine derivatives, D- or L-tryptophan derivatives, tetrazolyl(alkyl)-cyclohexyl-aminoacid derivatives, octahydrophenanthrene derivatives, benzomorphan, piperazinyl or piperidinyl-alkyl substituted isoxazole derivatives, decahydroisoquinoline-3-carboxylic ester or its amide preparation, compounds based on Conantokin-G peptide, 3-heterocyclyl-alkyl-benzopyran-2-one derivatives, phosphono-alkyl imidazo-pyrimidine carboxylic acid derivatives, amantadine, memantine, rimantidine, histogranin and analogues, nitrobenzoic acid derivatives, e.g 4-((2-methoxycarbonyl-4-nitrophenyl)methyl)piperazine carboxylic acid, diamine derivatives with selective sigma receptor affinity, remacemide (2-amino-N-(1,2-diphenyl-1-methylethyl)acetamide), phosphono-alkylidene- or phosphono-alkoxy-imino-piperidine acid, benzothiadiazine carboxylic acid derivatives, dihydro-benzothiadiazine dioxide carboxylic acid derivatives, 4-hydroxy 2(H) pyrrolone derivatives, quinoxaline derivatives, tetrahydro-imidazo(1,2-a)pyrimidines or their salts, 4-hydroxy-pyrrolo(1,2-b)pyridazin-2(1H)-one derivatives, nitroquinolone derivatives, 3-aryl-substituted 2(1H)quinolone, 2(1H)-quinolone, phosphonic acid quinoline-2-carboxylic acid derivatives, benzimidazole(s) carrying 2 acidic groups, N,N'-disubstituted guanidine derivatives, tricyclic quinoxalinediones, 2-(2,3-dicarboxycyclopropyl) glycine, isatine derivatives, 3-amino-indolyl-derivatives, 2-phenyl-1,3-propanediol dicarbamate (felbamate), benzomorphan derivatives, dihydrothienopyridine derivatives, (aminophenyl)-heteroaryl ethylamine, pyridazinedione derivatives, a 2H-1-benzopyran-2-one compound, a 4-sulphonylamino-quinoline derivative, R(plus)-3-amino-1-hydroxy-pyrrolidine-2-one, 2-carboxy indole, substituted. imino-methano dibenzo(A,D) cycloheptene derivatives, indole-hydrazone, piperazine derivatives, 4,6-disubstituted tryptophan and kynurenine derivatives, fluorenamine, diketo-pyridopyrazine derivatives or its salts, 2-amino-3,4-dioxo-1-cyclobutene derivatives, 2-acyl-amido derivatives of 3,4-dihydro-3-oxo-quinoxaline, benzimidazole phosphono-aminoacid derivatives, quinoxaline phosphono-aminoacid derivatives, piperazine, piperidine or pyrrolidone derivatives, its salts and isomeric forms including stereoisomers, 4-hydroxy-2(1H)-quinolinone derivatives, its salts and prodrugs, fused pyrazine derivatives, 2-phenyl or 2-thienyl-(2)-piperidine derivatives, 3-amido or 3-sulphamido-indolyl derivatives, 3-aryl-4-hydroxy-2-(1H)-quinolone derivatives, 2-heterocyclyl-2-hydroxy-ethylamine derivatives, 1-aryl-2-aminomethyl pyrrolidine, its optical isomers and acid-addn. salts, 4,6-dihalo indole-2-carboxylic acid derivatives, cyclic amino-hydroxamate derivatives, tetracyclic amine derivatives, 2,4-dioxo-1,2,3,4-tetrahydroquinoline derivatives, 2,4-dioxo-1,2,3,4-tetrahydroquinoline derivatives, 3-phosphonopiperidine and p-pyrrolidine derivatives, benzothieno(2,3-B)-pyrazine-2,3-(1H,4H)-dione, spiro dibenzosuberane derivatives, benzomorphan derivatives, preparation of 3,4-disubstituted 2-isoxazoline(s) and isoxazoles(s), 3-indolyl thio-acetate derivatives, arginine-derived nitric oxide biosynthesis inhibitors, dicyclic amine derivatives, spiroisoindole derivatives, imidazo(1,2-A)-pyridinylalkyl, 1,2,3,4-tetrahydro-9H-pyridoindole or benzothiophene derivatives, indole-2,3-dione-3-oxime derivatives, 1-aryl-2-(aminomethyl) cyclopropanecarboxamide derivatives, 4-phosphono-2-amino-alkenoic acid derivatives, naphthopyran derivatives, beta-ketone, beta oxime or beta hydrazine phosphonate, topa quinone aminoacid, kynurenic acid, quinoline- or thienopyridine-carboxylic acid derivatives, 10,5-(imino-methano)-10,11-dihydro-5H-dibenzo(A,D)cycloheptene or its derivatives, bicyclic amino-hydroxamate derivatives, indole-2-carboxylic acid derivatives, substituted adamantane derivatives, benzobicycloalkane derivatives, 2,4-disubstituted-1,2,3,4-tetrahydro-quinoline derivatives, dihydroalkyl-substituted-(immunomethano)-5H-dibenzo-cycloheptene, aryl-cyclohexylamine, N-substituted. benzobicycloalkane amine, isoquinoline phosphonates, N,N'-disubstituted.-guanidine, phosphonopropenyl piperidine carboxylic acid, (2R,3S,4S)-alpha-carboxy-cyclopropyl-glycine, pyrrolidine derivatives, dihydroxy-fused heterocyclyl quinoxaline derivatives, hydrogenated derivatives of MK 801 and analogues, 5-substituted 10,11-dihydro 5H-dibenzo(a,d)cycloheptene5,10-imine, 11-exo-hydroxy MK 801 preparations, tetra hydro-isoquinoline or 2-benzazepine derivatives, N-3-phenyl-propionyl-substituted. spermine or related polyamine derivatives, 4-amino-fluorene or its heterocyclic analogues, cyclooctane-imine derivatives, R-3-amino-1-hydroxy pyrrolidin-2-one or methionine hydroxamate, 10,11-dihydro-5H-dibenzo-cyclohepten-5,10-imine, polyhydro-10,11-dihydro-5H-benzo(a,d)cyclohepten-5,10 imine derivatives, 4-oxo-1,4-dihydroquinoline with 2-acidic groups, heterocyclyl-alkene-phosphonic acid, phosphono group-containing pyridine 2-carboxylic acid, alpha-amino-alpha-(3-alkylphenyl)alkyl ethanoic acid, its esters or amides, 10,11-dihydro-5H-dibenzo-A,D-cyclohepten-5,10-imine, phosphorus containing unsaturated amino acids or their salts, 5 substituted-1-,11-dihydro-5H-dibenzo-cyclohepten-5,10-imine or analogues, heterocyclic phosphonic acid derivatives or their salts, substituted 4-(aminocarbonyl-amino)quinoline derivatives, tricyclic quinoxaline derivatives, butyryl-tyrosine spermine or one of its analogues, tri- or tetra-substituted guanidine, quinoxalinylalkyl-aminoalkane phosphonic acid derivatives, 2-(aminophenyl)-3-(2-carboxy-indol-3-yl)-propenoic acid derivatives, 6-piperidinylpropionyl-2(3H)-benzoxazolone derivatives, 6-(3-[4-(4-fluorobenzyl)piperidin-1-yl]propionyl)-3H-benzoxazol-2-one or its salts, imidazo(1,2-a)pyridine, tetrahydroquinoline derivatives or their salts, 2-methyl-5,8-substituted 2,3,4,5-tetra- or 2,3,4,4a,5,9b-hexahydro-1H-pyrido[4,3-b]indole, 3-aminoindolyl, 6-pyrrolyl-quinoxaline-2.3-dione derivatives, imidazolyl-(mercaptoalkyl)-quinoxalinedione, 3-amidoindolyl derivatives, heterocyclyl-imidazoloquinoxalinone, naphthyl-substituted alpha-amino acid derivatives, 5-hetero-aryl-2,3-quinoxaline-dione derivatives, quinoxaline derivatives, 5H,10H-imidazo indeno 4-pyrazinone derivatives, hydroxy-(aryl-substituted phenyl)-quinolone, imidazo indolo pyrazinone derivatives, ((phenyl-amino)-(m)ethyl)-pyridine derivatives, tetrahydroisoquinoline derivatives, 4-substituted piperidine analogues, 2-substituted piperidine derivatives, tri- or tetra-substituted guanidine derivatives, 3-hydroxy-4-imidazolidinone, 3-aminoquinoxalin-2-one derivatives, 1-amino-1-cyclobutanecarboxylic acid, thiamorphinan derivatives, pyrido[4,3-b]indole derivatives, 4-phenyl carbamoyl methylene tetrahydro quinoline-2-carboxylic acid or derivatives thereof, (3R,4S)-3-(4-(4-fluorophenyl)-4-hydroxy-piperidin-1-yl)-chroman-4,7-diol, indeno-pyrazin-4-one, 2,3-dioxo-1,2,4,5-tetrahydro-quinoxalinyl derivatives, 4,5-bridged quinoxalinedione or quinolone, (1S,2S)-1-(4-hydroxyphenyl)2-(4-hydroxy 4-phenyl piperidin-1-yl) 1-propanol methane sulphonate trihydrate, 4-sulphanimide-quinoline derivatives, methanobenzocyclodecen-13-amine, quinoxalinyl-(alkane, alkene, or alkyne)-phosphonic acid derivatives and esters, diarylalkylamine related to spider and wasp venom toxins, piperazine R-alpha-carboxylic acid derivatives, imidazo-indeno-pyrazin-4-one derivatives, pyridazino-quinoline derivatives, 1-substituted or 1,3-di-substituted 1,3-diarylguanidine, aza-cycloalkyl-fused quinoxaline-dione, 3-substituted 2-carboxy-indole derivatives or intermediates, (2R)-N-trityl-4-oxo-5-(dimethyl phosphono)-nor-valinate ester, kynurenic acid derivatives, indole carboxylic acid derivatives, 6-(tetrazolyl or isoxazolyl)-decahydroisoquinoline-3-carboxylic acid derivatives, phenyl- or pyridinyl-thienopyridinone derivatives, fused cycloalkyl-quinoxaline-dione derivatives, pyridazino-quinoline derivatives, 1-alpha-amino-3-biphenyl-propanoic acid derivatives, 3-(Indol-3-yl) propenoic acid derivatives, spiro-heterocycle-imidazo-indeno-pyrazine-4-one derivatives, 2-heterocyclyl-3-indolylpropenoic acid derivatives, piperidinoalkyl heterocyclic ketone, pyrrolyl-tetrahydro-benzoquinoxaline-dione derivatives, 7-imidazolyl or dialkylamino, tetrahydroquinoxaline dione, dibenzocycloheptene, quinoxaline derivatives, aryl-thio-quinoxaline derivatives, heterocyclic substituted imidazolo-quinoxaline derivatives, 1,4-dihydroquinoxaline-2,3-dione derivatives, oxa- or thia-aliphatically bridged quinoxaline derivatives, aza-aliphatically bridged quinoxaline-2,3-dione, 3-amido- or 3-sulphamido-indole, 3,5-disubstituted phenyl-naphthalene derivatives, imidazo (1,2-a)indeno (1,2-e) pyrazine-2-carboxylic acid derivatives, 3-phenyl-fused ring pyridine-dione derivatives, 2-phenyl-pyridazino-indole-dione derivatives, 4,6-disubstituted kynurenine, phosphono derivatives of imidazo(1,2-a)pyrimidine-2-carboxamide, tetrahydro-quinoxaline-dione derivatives with N-(alkyl)carbonyl-amino- or ureido group, tryptophan derivatives, hetero-aliphatic or hetero-araliphatic substituted quinolone derivatives, imidazo-pyridine dicarboxylic acid derivatives, compositions containing pyrazolo-quinoline derivatives, ethanodihydrobenzoquinolizinium salt, oxopyridinylquinoxaline derivatives, indeno-triazolo-pyrazin-4-one derivatives, imidazo-indeno-pyrazinone derivatives, imidazo-indeno-pyrazin-4-one derivatives, imidazo(1,2-a)pyrazine-4-one derivatives, 5H-indeno-pyrazine-2,3-dione derivatives, phenyl-aminoalkyl-cyclopropane N,N-diethyl carboxamide, dexanabinol derivatives, substituted chroman derivatives, sulphonamide quinazoline-2-4-dione, 6- and 8-aza-, and 6,8-diaza-1,4-dihydro-quinoxaline-2,3-dione derivatives, substituted quinoline derivatives, tetrazolylalkyl cyclohexyl aminoalkanoic acid, tricyclic indole 2-carboxylic acid derivatives, 6-substituted-7H-imidazo-8-pyrazinone derivatives, tricyclic pyridazinopyridine derivatives, N-substituted heterocyclylidenemethyl-indole carboxylic acid derivatives, 3-aza-8-substituted-bicyclo(3.3.0)octane-2-carboxylic acid derivatives, ethano-heterocyclo-isoquinolinium, phenyl alkanolamine derivatives, dihydrobenzothiadiazinedioxide carboxylic acid derivatives, methyl-butenylmethyl(hydroxy-propyl)carbazoledione, imidazo pyrazinone derivatives, imidazo-(1,2-a)pyrazine-4-one, benzazepine-dione derivatives, disulfiram, 3-(indol-3-yl)-propenoic acid derivatives, 1,2,3,4-tetrahydro-quinoline-2,3,4-trione-3 or 4-oxime, 2-amino-2-phenyl(alkyl)-acetic acid derivatives, 6-halo-tryptophan or a 4-halo-kynurenine, 6-tetrazolyl or isoxazolyl-decahydro-isoquinoline-3-carboxylic acid derivatives, or imidazolylbenzene or salts thereof.

F. NMDA Receptor Channel Blockers

NMDA receptor channel blockers refer to compounds that reduce the permeability of channels associated with the NMDA receptor to cations (preferably to $Na^+$, $K^+$ and $Ca^{2+}$ ions). NMDA receptor channel blockers can therefore be used to prevent a signal being transmitted due to ionic flux that would otherwise occur when glutamate binds to the NMDA receptor.

NMDA receptor channel blockers include i.e. magnesium, dizocilpine, phencyclidine, ketamine, memantine, tiletamine, budipine, flupirtine, 1-[1-(2-thienyl)cyclohexyl]piperidine (TCP), (+)-(3S,4S)-7-hydroxy-delta6-tetrahydrocannabinol-1,1-dimethylheptyl (HU211).

G. Glutamate Release Inhibitors

Such agents decrease the release of glutamate from nerve endings and prevent glutamate from binding to either AMPA, kainate, or NMDA binding sites and from triggering the signal that would occur as a result of binding of glutamate to these binding sites.

Glutamate release inhibitors include e.g. riluzole, lamotrigine, diphenylhydantoin, tetrodotoxin, agatoxin-glutamate-release-inhibitor (AG-GI), [5-(2,3,5-trichlorophenyl)]-2,4-diamino-pyrimidine (BW1003C87), (R)-(−)-5-methyl-1-nicotinoyl-2-pyrazoline (MS-153) and 4-amino-2-(4-methyl-1-piperazinyl)-5-(2,3,5-trichlorophenyl) pyrimidine (BW619C89).

H. Glycine Release Inhibitors

Such agents decrease the release of glycine from nerve endings and prevent glycine from binding to glycine B binding sites and from triggering the signal that would occur as a result of binding of glutamate to NMDA binding site.

I. Glutamate Synthesis Inhibitors and Drugs Interfering With Glutamate Metabolism Such compounds block synthesis of glutamate or increase metabolism of glutamate preventing activation of either AMPA, kainate or NMDA binding sites.

Compounds interacting with glutamate synthesis or metabolism and preventing activation of either AMPA, kainate or NMDA receptors include e.g. gabapentin, L-canaline, phenylsuccinate, spermidine, putrescine, gentamicin, orthovanadate, vanadyl sulphate, vanadyl acetylacetonate, methionine sulphoximine, chloroquine, amodiaquine, quinacrine, chinidine, chinine, α-monofluoromethylputrescine and (R,R)-delta-methyl-α-acetylenic-putrescine.

J. Compounds Accelerating Glutamate Uptake

Such agents decrease synaptic concentration of glutamate by activating uptake mechanisms for glutamate preventing activation of either AMPA, kainate or NMDA receptors.

Compounds accelerating glutamate uptake mechanisms include e.g. γ-glutamyl-transpeptidase.

K. Agents That Interact With Glutamate and Prevent its Binding to its Receptors

Such agents include i.e. glutamate partial agonists which activate glutamate receptors by themselves but are less active than glutamate at these receptors and therefore decrease activation of these receptors by glutamate at physiological and excessively high concentrations or molecules binding to glutamate which change conformational state of glutamate and therefore decrease its binding capability to its receptors.

Glutamate partial agonists are e.g. D-serine, D-cycloserine, γ-L-glutamylglutamate, N-phthalamoyl-L-glutaminic acid, (R,S)-2-amino-3-[5-tert-butyl-3-(phosphonomethoxy)-4-isoxazolyl]propionic acid, α-N-acetylaspartylglutamate, 1-aminocyclopropanecarboxylic acid, aminocyclobutane cyrboxylic acid, (+,R)-3-amino-1-hydroxy-2-pyrrolidine (HA966) and D,L-threo-3-hydroxyasparate.

Furthermore such agents include soluble forms of NMDA, kainate or AMPA receptors or parts thereof. These soluble forms can be used to circulate and to bind to glutamate and therefore decrease its binding capability to the receptors. Membrane bound forms of the glutamate receptors may also be incorporated into liposomes, circulate and bind to glutamate so as to prevent it binding to its receptors.

L. Agents That Interact With Glutamate Transporter Systems

Such agents accelerate glutamate transporter function and decrease glutamate concentration at its receptors preventing activation of either AMPA, kainate or NMDA receptors.

Such agents include e.g. 12-O-tetradecanoylphorbol-13-acetate, phorbol-12-myristate 13-acetate.

M. Antibodies Interacting With AMPA Receptors or With Glutamate

The AMPA, kainate or NMDA receptors or a part or parts of them, or glutamate can be used for raising antibodies that bind thereto. Preferred antibodies bind specifically to either AMPA, kainate or NMDA receptor or a part thereof, or to glutamate. The antibodies may be monoclonal or polyclonal. Polyclonal antibodies can be raised by stimulating their production in a suitable animal host (e.g. a mouse, rat, guinea pig, rabbit, sheep, goat or monkey) when either AMPA, kainate or NMDA receptor, or a part thereof, or glutamate is injected into the animal. If necessary an adjuvant may be administered together with the AMPA, kainate or NMDA receptor, or a part thereof, or with glutamate. In addition to whole antibodies, antagonists of the present invention include derivatives thereof.

DISCLOSURE OF THE INVENTION

The present inventor has provided evidence that glutamate antagonists supress tumor growth. This invention represents a major advance in the treatment of cancer.

According to the present invention, glutamate antagonists which block glutamate function at NMDA, AMPA or kainate receptor complexes, when used alone or in combination with cytostatic agents or physical measures, such as irradiation, will result in anticancer activity superior to that achieved with cytostatic agents or physical measures alone.

The present invention will now be described by way of example only, with reference to the accompanying drawings, wherein:

EXAMPLES

The tumor cell lines used in the context of this invention have been obtained from human tumors. Agents active against tumor growth in vitro have proved to also be effective anticancer agents in vivo.

The surprising observation that glutamate antagonists have antiproliferative actions in tumor cells and that the tumoricidal effect of three different cytostatic agents, cisplatin, vinblastin and thiotepa is significantly enhanced by two different AMPA antagonists, GYKI 52466 and NBQX (2,3-dihydroxy-6-nitro-7-sulfaoylbenzo-(F)-quinoxaline) and the NMDA antagonist MK 801 is described in the following paragraphs.

Cell lines and Culture.

Human neuroblastoma (SKNAS), human rhabdomyosarcoma/medulloblastoma (TE671), human brain astrocytoma (MOGGCCM), human thyroid carcinoma (FTC238), human Caucasian lung carcinoma (A549), humans Caucasian colon adenocarcinoma (LS180) and human breast carcinoma (T47D) were obtained from European Collection of Cell Cultures (ECACC), Center for Applied Microbiology & Research, Salisbury, UK.

SKNAS, TE671, T47D, LS180 were grown in 1:1 mixture of Dulbecco's Modified Eagle's Medium (DMEM; D 6421, Sigma, $Ca^{2+}$-concentration 1.05 mM) and Nutrient Mixture F-12 Ham (Ham's F-12; Sigma) supplemented with 10% Foetal Bovine Serum (FBS) (GIBCO). FTC238 was grown in the same culture medium suplemented with 5% FBS. MOGGCCM and A549 were grown in 2:1 mixture of DMEM (D 6046, Sigma, $Ca^{2+}$-concentration 1.8 mM): Ham's F-12 supplemented with 10% FBS. Cultures were kept at 37° C. in a 95% air-5% $CO_2$ atmosphere. As $Ca^{2+}$-free medium, minimum essential medium M8167 from Sigma was used.

Assessment of cell viability.

The yellow tetrazolium salt MTT (3-4,5-dimethylthiazol-2-2,5-diphenyltetrazolium bromid) is metabolized by viable, metabolically active cells to purple formazan crystals. Tumor cells grown in 96 well multiplates were incubated over 4 hrs with MTT solution (Cell proliferation kit I, Boehringer Mannheim, Germany). Formazan crystals were solubilized overnight, according to the manufacturer's instructions, and the product was quantified spectrophotometrically by measuring absorbance at 570 nm wave length using a VICTOR Multilabel Counter (Wallach).

Assessment of tumoricidal effect.

Quantitation of cell death was performed at 24, 48 or 72 hrs after exposure to the agents of interest following staining of the cells with trypan blue. This stain is taken up by necrotic cells. The numbers of necrotic cells/100 counted cells served as quantitative measure for tumoricidal effect (% of tumor cell death). For each agent or combination of agents and each time point 5 wells were analysed. Comparisons between groups was performed by means of Student's t-test.

Exposure to agents.

Tumor cells were exposed to the following agents and concentrations: MK 801 (10-500 µM), GYKI 52466 (10-500 µM), Cisplatin (10 µM), Vinblastin (1 µM), Thiotepa (10 µM) alone or in combination with MK 801 (10 µM), GYKI52466 (10 µM) or NBQX (10 µM).

Results

Figure 1:
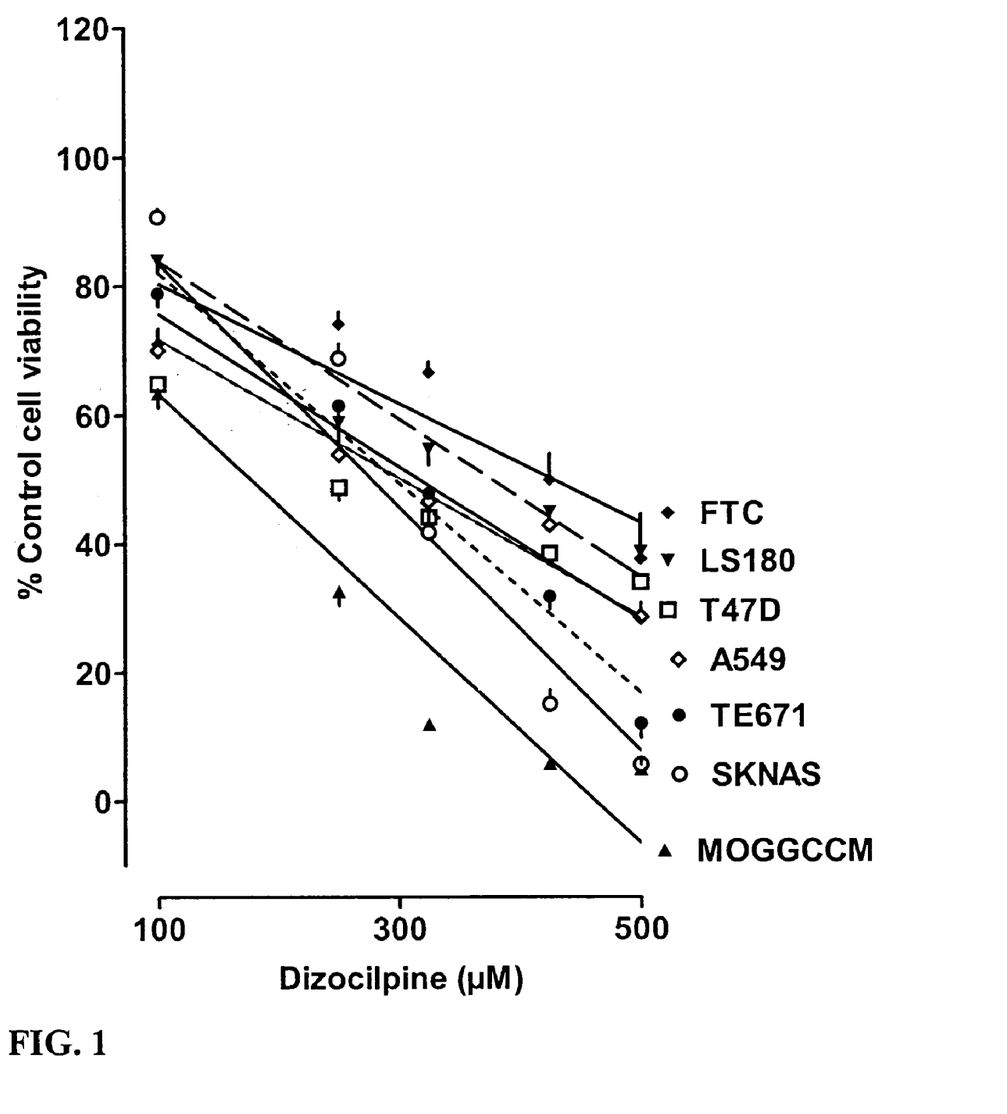
FIG. 1: The NMDA antagonist (+)dizocilpine exerts a concentration dependent antiproliferative effect in human tumor cell lines. Cells were exposed to either culture medium alone (control) or dizocilpine (10-500 µM) over 96 hrs and viability was measured photometrically by means of the MTT assay. Data represent mean normalized optical densities ±SEM of 6-8 measurements and were analyzed by means of linear regression. Abbreviations. SKNAS: human neuroblastoma; TE671: human rhabdomyosarcoma/medulloblastoma; MOGGCCM: human brain astrocytoma; FTC238: human thyroid carcinoma; A 549: human Caucasian lung carcinoma; LS180: human Caucasian colon adenocarcinoma; T47D: human breast carcinoma.
Figure 2:
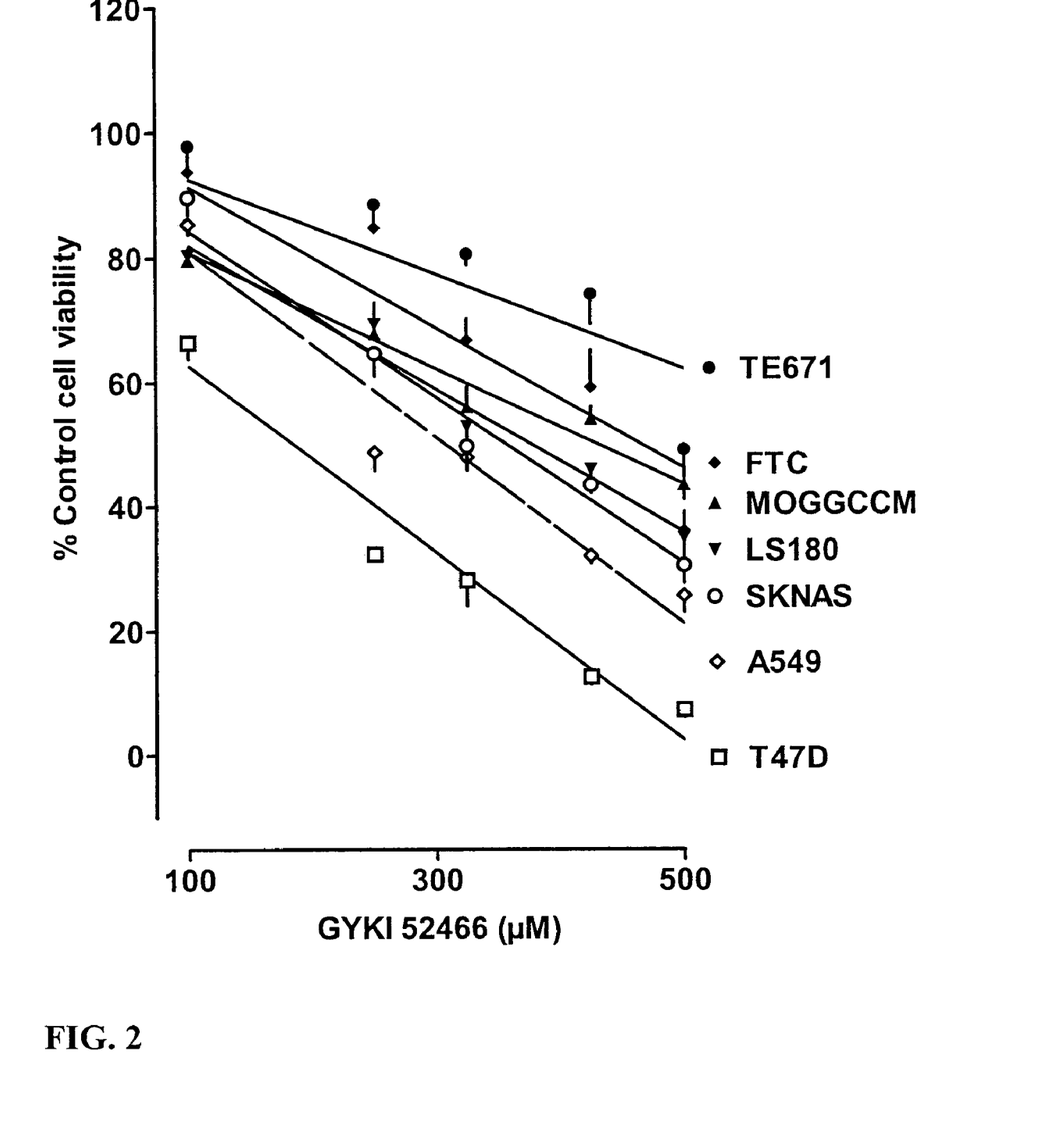
FIG. 2: The AMPA antagonist GYKI52466 exerts a concentration dependent antiproliferative effect in human tumor cell lines. Cells were exposed to either culture medium alone (control) or GYKI52466 (10-500 µM) over 96 hrs and viability was measured photometrically by means of the MTT assay. Data represent normalized optical densities ±SEM of 6-8measurements and were analyzed by means of linear regression. Abbreviations. SKNAS: human neuroblastoma; TE671: human rhabdomyosarcoma/medulloblastoma; MOGGCCM: human brain astrocytoma; FTC238: human thyroid carcinoma; A 549: human Caucasian lung carcinoma; LS180: human Caucasian colon adenocarcinoma; T47D: human breast carcinoma.

The NMDA antagonist MK801 and the AMPA antagonists GYKI52466 displayed a significant concentration-dependent antiproliferative effect in different tumor cell lines (FIGS. 1 and 2).

Figure 3:
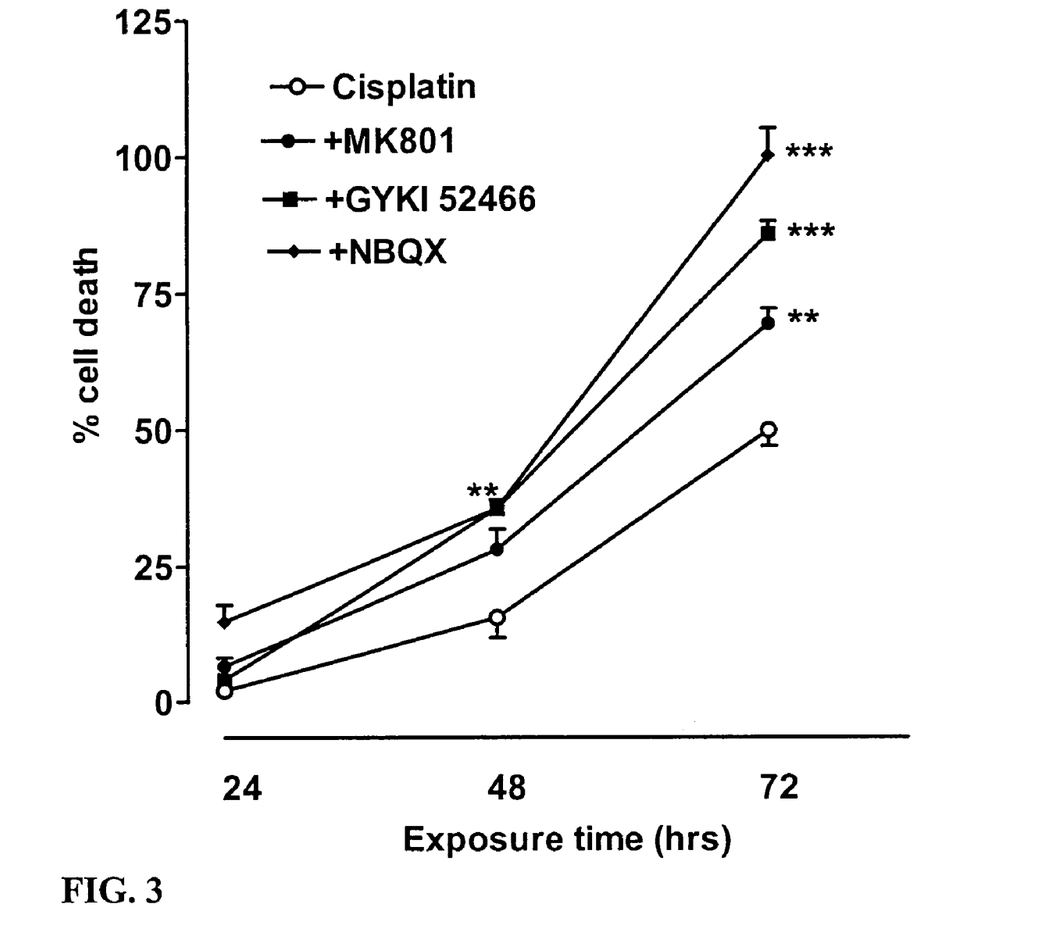
FIG. 3 shows that the the NMDA antagonist MK801 (10 µM), and the AMPA receptor antagonists GYKI 52466 (10 µM) or NBQX (10 µM) significantly increase toxicity of cisplatin (10 µM) against the human neuroblastoma cell line SK-N-AS. Data represent the mean±SEM of necrotic cells visualized by trypan blue staining (n=5/group). The potentiating effect of all three glutamate receptor antagonists was most prominent after an exposure time of 72 h. *$P<0.05$; $P<0.01$; *$P<0.001$, Student's t test.
Figure 4:
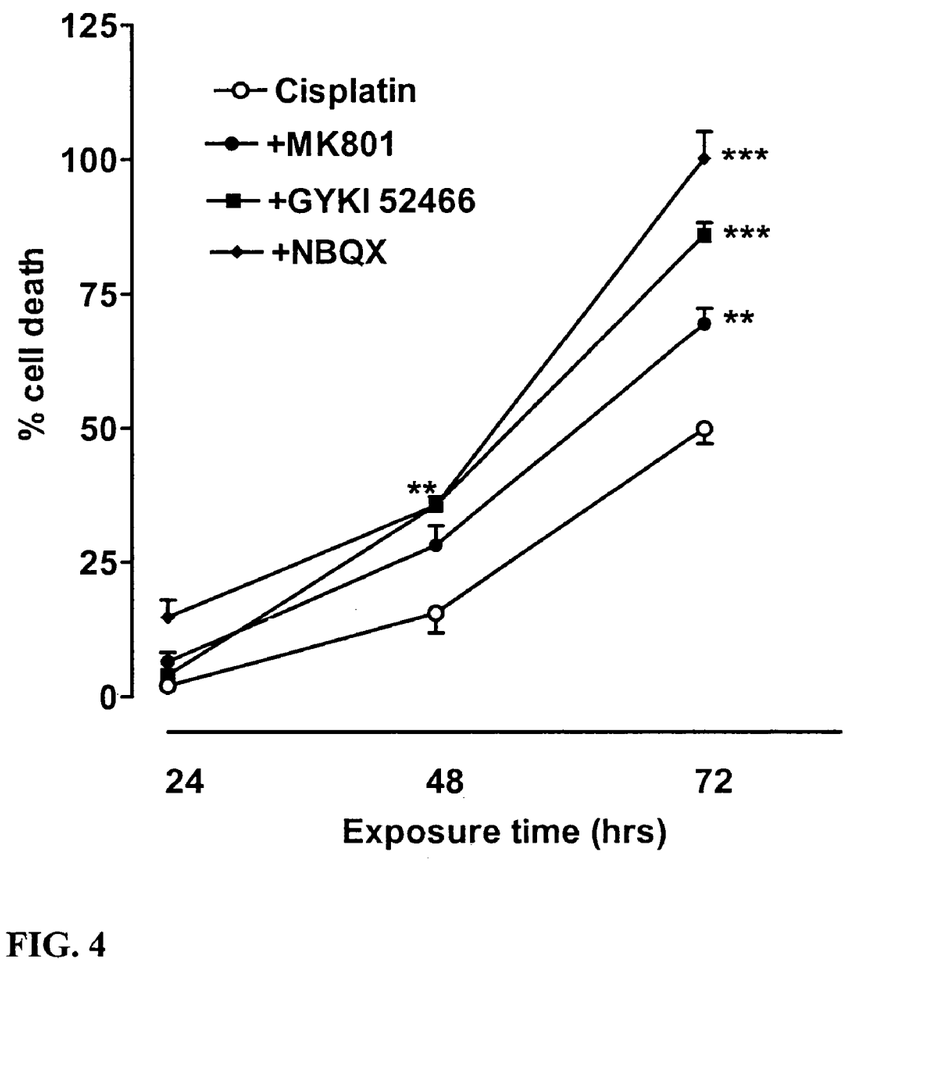
FIG. 4 shows that MK801 (10 µM), GYKI 52466 (10 µM) or NBQX (10 µM) potentiate toxicity of thiotepa (10 µM) against the tumor cell line SK-N-AS. Data represent the mean±SEM of necrotic cells visualized by trypan blue staining (n=5/group). The potentiating effect of the NMDA- and both AMPA antagonists is most prominent after an exposure time of 72 h. *$P<0.05$; $P<0.01$; *$P<0.001$, Student's t test.
Figure 5:
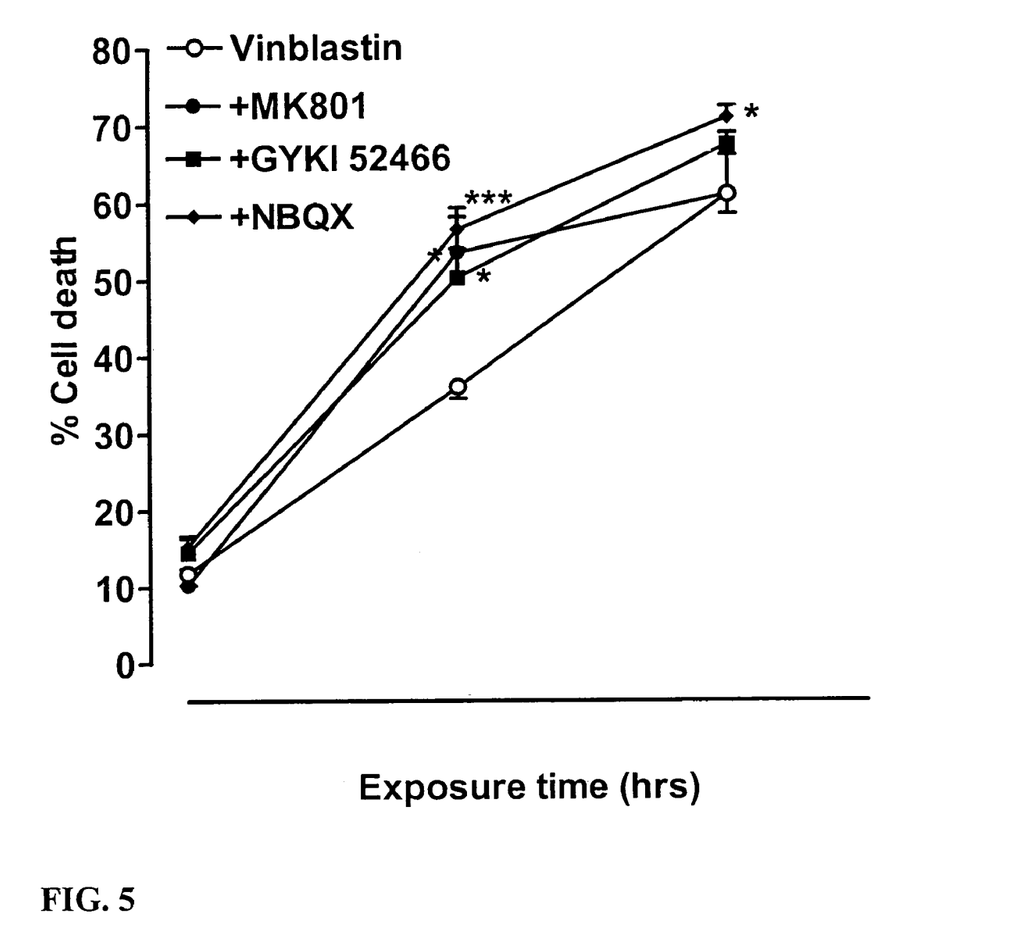
FIG. 5 shows that MK 801 (10 µM), GYKI 52466 (10 µM) or NBQX (10 µM) potentiate toxicity of vinblastin (1 µM) against the tumor cell line SK-N-AS. Data represent the mean±SEM of necrotic cells visualized by trypan blue staining (n=5/group). The potentiating effect of the NMDA- and both AMPA antagonists is most prominent after an exposure time of 48 hrs. *$P<0.05$; $P<0.01$; *$P<0.001$, Student's t test.

In addition, NMDA and AMPA antagonists enhanced tumoricidal effect of cytostatic agents (FIGS. 3-5). Each of the cytostatic agents tested produced a significant tumoricidal effect on its own at the concentrations used, which reached a peak for all three agents after 72 hrs exposure time. The NMDA antagonist MK 801 and the AMPA antagonists GYKI 52466 and NBQX significantly ($P<0.05$-$0.001$) potentiated tumoricidal effect of cisplatin, vinblastin and thiotepa when used in combination with the cytostatic agents. This potentiation of the tumoricidal effect of the cytostatic agents by the NMDA and the AMPA antagonists was most pominent after an exposure time of 72 hrs for cisplatin and thiotepa and 48 hrs for vinblastin (FIGS. 3-5).

BEST MODE FOR CARRYING OUT THE INVENTION

Use of various tumor cell lines in culture and exposure of the tumor cells over 72-96 hrs either to glutamate antagonists alone or to glutamate antagonists in combination with cytostatic agents is required and should be performed as described in "Disclosure of the Invention." Quantification of cell death can be performed by means of trypan blue staining and direct counting of the degenerated cells in the microscope. Quantification of metabolically active cells can be performed photometrically by means of the MTT-assay. Culture techniques, trypan blue staining and photometric MTT-measurements are known and established methods which can easily be carried out in every cell culture laboratory.

INDUSTRIAL APPLICABILITY

Therapeutic Use

Glutamate inhibitors of the present invention may be used in human and veterinary medicine. Treatments may be prophylactic or may be in respect of existing conditions.

The glutamate antagonists may be used in the manufacture of a medicament for treating cancer. The term cancer is used herein to include any disorder that results from abnormal and uncontrolled cell growth with resulting invasion and destruction of neighbouring tissue which can but must not set metastases to distant tissues. The present invention includes within its scope pharmaceutically acceptable compositions useful in treating cancer which comprise a glutamate antagonist of the present invention. The antagonist will usually be provided in combination with a pharmaceutically acceptable carrier. It may be used in any suitable form, provided that it can act in inhibiting the interaction of glutamate with the AMPA, KA or NMDA/glycine/polyamine receptor complex. Pharmaceutically acceptable salts may also be used.

Pharmaceutical compositions within the scope of the present invention may include one or more of the following: preserving agents, solubilising agents, stabilising agents, wetting agents, emulsifiers, sweeteners, colorants, odourants, salts, buffers, coating agents or antioxidants. They may contain a further therapeutically active agent in addition to a antagonist of the present invention. The further therapeutically active agent may be a cytostatic agent, an immunomodulating agent or physical measures such as irradiation, photomodulation or hyperthermia. The agents of present invention can also be combined with mono- or polyclonal antibodies, antisense therapeutics, cancer vaccines, or gene therapy.

The combination of an antagonist of the present invention and a further therapeutically active agent may be used simultaneously, separately or sequentially to treat cancer. It may provide synergistically effective combination. A pharmaceutical composition within the scope of the present invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) routes. Such a composition may be prepared by any method known in the art of pharmacy, for example by admixing one or more active ingredients with a suitable carrier. Preferably it will be provided in unit dosage form. It will normally be provided in a sealed, sterile container—e.g. in an ampoule, a vial, a bottle, a blister pack, or etc. Different drug delivery systems can be used to administer pharmaceutical compositions of the present invention, depending upon the desired route of administration. Such systems include aerosols, tablets, capsules, lozengers, pastilles, powders, solutions, suspensions, syrups, ointments, pastes, oils, suppositories, enemas, pessaries, tampons, sprays, nebulizers, injectable compositions, etc.

Dosages of the inhibitors of the present invention can vary between wide limits, depending upon the nature of the treatment and the age and condition of the individual to be treated. However, a daily dosage of from 0.01 mg to 1000 mg, preferably of from 0.5-200 mg may be suitable. The dosage may be repeated as often as appropriate. If side-effects develop, the amount and/or frequency of the dosage can be reduced, in accordance with good clinical practice.

Diagnostic Use

Diagnostic use is possible for testing whether a form of cancer is susceptible to treatment with glutamate antagonists. This testing would involve isolation and culturing of tumor cells and subsequently testing tumoricidal effect of glutamate antagonists alone or in combination with cytostatic agents, or immunomodulating agents, or physical measures such as irradiation, photomodulation, or hyperthermia.

The invention claim is:

1. A method of treating cancer comprising administering to a patient in need thereof an inhibitor of the interaction of glutamate with the Kainate receptor complex, wherein
    the inhibitor is 2,3-dihydroxy-6-nitro-7-sulfamoyl-benzo(F)quinoxaline(NBQX), 6,7-dinitro-quinoxaline-2,3-dione (DNQX), 6-nitro-7-cyano-quinoxaline-2,3-dione (CNQX), 6-(1-imidazolyl)-7-nitro-quinoxaline-2,3(1H,4H)-dione (YM90K), [2,3-dioxo-7(1H-imidazol-1-yl)-6-nitro-1,2,3,4-tetrahydro-1-quinoxaliny]-acetic acid monohydrate (YM872), (3RS,4aRS,6RS,8aRS)-6-(2-(1H-tetrazole-5-yl)ethyl)-decahydroiso-quinoline-3-carboxylic acid (LY293558), 9-methyl-amino-6-nitro-hexahydro-benzo(F)quinoxalinedione (PNQX), 8-methyl-5-(4-(N,N-dimethylsulphamoyl)phenyl)-6,7,8,9-tetra-hydro-1H-pyrrolo[3,2h]-isoquinoline-2,3-dione-3-O-(3-hydroxybutyric acid-2-yl)oxime (NS 1209), 6,7-dichloro-2-(1H)-quinolinone-3-phosphonate (S17625-2), [1,2,3,4-tetrahydro-7-morpholinyl-2,3-dioxo-6-(trifluoromethyl)quinoxalin-1-yl]methyl-phosphonate (ZK200775), 1-(aminophenyl)-4-methyl-7,8-methylenedioxy-5H-2,3-benzodiazepine (GYKI 52466), γ-D-glutamylaminomethylsulphonate (GAMS), γ-D-glutamylglycine; or a Kainate receptor channel blocker.

2. A method according to claim 1, wherein cancer includes any disorder that results from abnormal and uncontrolled cell growth with resulting invasion and destruction of neighboring tissue which optionally sets metastases to distant tissues.

3. A method according to claim 1, wherein the inhibitor is 2,3-dihydroxy-6-nitro-7-sulfamoyl-benzo(F)quinoxaline (NBQX), 6,7-dinitro-quinoxaline-2,3-dione (DNQX), 6-nitro-7-cyano-quinoxaline-2,3-dione (CNQX), 6-(1-imidazolyl)-7-nitro-quinoxaline-2,3(1H,4H)-dione (YM90K), [2,3-dioxo-7(1H-imidazol-1-yl)-6-nitro-1,2,3,4-tetrahydro-1-quinoxalinyl]-acetic acid monohydrate (YM872), (3RS,4aRS,6RS,8aRS)-6-(2-(1H-tetrazole-5-yl)ethyl)-decahydroiso-quinoline-3-carboxylic acid (LY293558), 9-methyl-amino-6-nitro-hexahydro-benzo(F)quinoxalinedione (PNQX), 8-methyl-5-(4-(N,N-dimethylsulphamoyl)phenyl)-6,7,8,9-tetra-hydro-1H-pyrrolo[3,2h]-isoquinoline-2,3-dione-3-O-(3-hydroxybutyric acid-2-yl)oxime (NS 1209), 6,7-dichloro-2-(1H)-quinolinone-3-phosphonate (S17625-2), [1,2,3,4-tetrahydro-7-morpholinyl-2,3-dioxo-6-(trifluoromethyl)quinoxalin-1-yl]methyl-phosphonate (ZK200775), 1-(aminophenyl)-4-methyl-7,8-methylenedioxy-5H-2,3-benzodiazepine (GYKI 52466), γ-D-glutamylaminomethylsulphonate (GAMS), or γ-D-glutamylglycine.

4. A method according to claim 1, wherein the inhibitor is a Kainate receptor channel blocker.

5. A method according to claim 4, wherein the Kainate receptor channel blocker is Joro spider toxin, NSTX spider toxin, or argiotoxin.

6. A method according to claim 5, wherein the cancer treated is a solid tumor.

7. A method according to claim 1, wherein the cancer treated is neuroblastoma.

8. A method according to claim 1, wherein the cancer treated is rhabdomyosarcoma.

9. A method according to claim 1, wherein the cancer treated is brain glioma.

10. A method according to claim 1, wherein the cancer treated is thyroid cancer.

11. A method according to claim 1, wherein the cancer treated is lung cancer.

12. A method according to claim 1, wherein the cancer treated is colon cancer.

13. A method according to claim 1, wherein the cancer treated is breast cancer.

14. A method according to claim 1, wherein the cancer treated is astrocytoma.

15. A method according to claim 1, wherein the cancer treated is a solid tumor.

* * * * *